United States Patent [19]

Kastendieck et al.

[11] Patent Number: 4,703,879
[45] Date of Patent: Nov. 3, 1987

[54] NIGHT VISION GOGGLE HEADGEAR

[75] Inventors: William A. Kastendieck, Wylie; Richard T. Hart, Garland, both of Tex.

[73] Assignee: Varo, Inc., Garland, Tex.

[21] Appl. No.: 808,152

[22] Filed: Dec. 12, 1985

[51] Int. Cl.⁴ .............................................. A42B 1/241
[52] U.S. Cl. .......................................... 224/181; 2/6; 350/143
[58] Field of Search ....................... 224/181, 909, 908; 2/6, 418, 419, 420, 422; 350/143; 351/245; D2/231, 230, 233

[56] References Cited

U.S. PATENT DOCUMENTS

| D. 209,116 | 10/1967 | Treutelaar . | |
|---|---|---|---|
| D. 237,843 | 12/1975 | Peterson et al. . | |
| 1,305,852 | 6/1919 | Widmer | 224/181 X |
| 2,254,669 | 9/1941 | Turner | 2/233 |
| 2,270,931 | 1/1942 | Corcoran . | |
| 2,765,398 | 10/1956 | Mays . | |
| 2,848,924 | 8/1958 | Potez . | |
| 2,867,812 | 1/1959 | Roth et al. . | |
| 3,010,109 | 11/1961 | Gray | 2/6 |
| 3,040,741 | 6/1962 | Carolan . | |
| 3,108,282 | 10/1963 | Rehman et al. . | |
| 3,409,909 | 11/1968 | Scott et al. . | |
| 3,425,769 | 2/1969 | Stone . | |
| 3,739,961 | 6/1973 | Soukeras | 224/205 X |
| 3,833,935 | 9/1974 | Ansite et al. . | |
| 4,136,403 | 1/1979 | Walther et al. . | |
| 4,270,679 | 6/1981 | Gildea et al. . | |
| 4,449,787 | 5/1984 | Burbo et al. . | |
| 4,457,461 | 7/1984 | Docking et al. . | |
| 4,463,252 | 7/1984 | Brennan et al. . | |

Primary Examiner—Henry J. Recla
Assistant Examiner—Robert M. Petrik
Attorney, Agent, or Firm—Jerry W. Mills; Roger N. Chauza

[57] ABSTRACT

A headgear (10) for supporting a night vision goggle (12) to the head of a wearer. A flexible temporal strip (18) is joined to a flexible crown strip (20) in the forehead region, at which juncture a pair of integral rails (74, 76) suspend the goggle (12) therefrom. The temporal strip (18) and crown strip (20) include free ends which are directed toward the posterior of the cranium (22) and are connected by straps (36, 46, 48) to a webbed pad (38) which engages the occipital protuberance to prevent forward rotation of the headgear (10) due to the weight of the goggle (12). Lower girth straps (68, 69) maintain attachment of the headgear (10) to the cranium (22) and further aid in antirotational movement.

31 Claims, 9 Drawing Figures

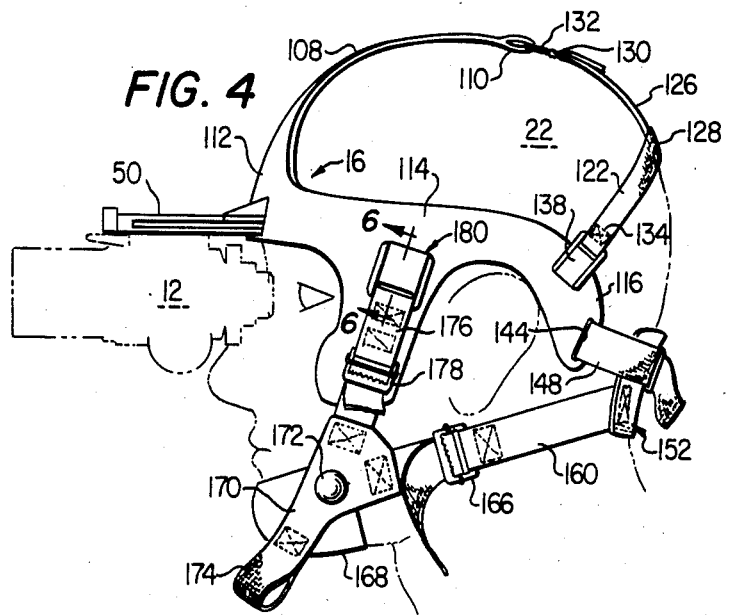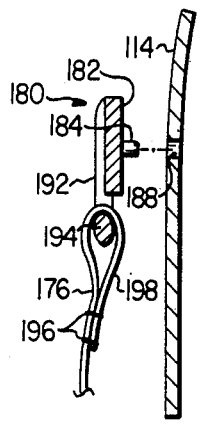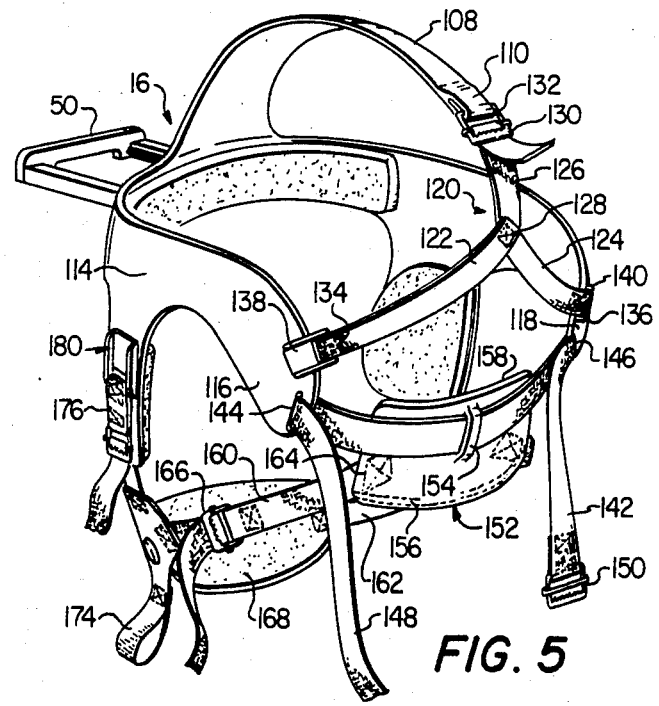

NIGHT VISION GOGGLE HEADGEAR

BACKGROUND OF THE INVENTION

Night vision goggles are standard equipment used by military personnel to facilitate nocturnal activities. Such goggles are adapted for amplifying faint illuminations reflected from distant objects so that the objects are easily observable in the dark. Reflections of starlight from an object are sufficient to distinguish the object from its surroundings. A night vision goggle employing such a principle is disclosed in U.S. Pat. No. 4,463,252.

Night vision goggles are typically worn attached to a helmet, face frame or other similar equipment. This enables the wearer the free use of both hands, whereby a person is not encumbered by having to hold the goggle in one hand and perform other tasks with the other hand. Face frame apparatus adapted for such use is also disclosed in the noted patent.

While prior face frames supporting night vision goggles have been used with a certain degree of success, there are various inherent shortcomings. Most notably, conventional night vision goggle face frames are extremely difficult to use in conjunction with a gas mask, or a head mounted microphone, or to conduct basic functions such as eating. Moreover, the multiplicity of straps used to pull the plastic face frame flush against a wearer's face can become easily entangled, thereby making application difficult.

Another shortcoming is that a single plastic face frame must accommodate the shape of all wearers. A universally shaped plastic face frame is not possible as the variations of facial shapes are too varied and different. An additional disadvantage with the use of a plastic face frame is that the weight of the night vision goggle concentrates most of the pressure on the lower facial area of the wearer. This not only makes verbal communications difficult, but also causes a high degree of neck strain when worn for extended periods of time. The lower facial pressure can be relieved by tightening the upper straps on the face frame; however, this can lead to restriction of blood flow to the head and result in a headache.

From the foregoing, it may be seen that a need has arisen for a goggle headgear which is comfortable, and easily and quickly donned. There is an additional need for a goggle headgear which is attachable to a part of the cranium which is more universal in size and shape than the facial area. There is a related need for a goggle headgear which distributes pressure evenly over the cranial crown area.

SUMMARY OF THE INVENTION

The invention described herein substantially eliminates or reduces the shortcomings of the night vision goggle face frames heretofore known.

In accordance with the preferred embodiment of the present invention, there is provided a molded plastic headpiece which rests on the cranial crown. Included also is a posterior strap engageable with the cranial occipital bone so as to provide a comfortable headgear with a high degree of stability for supporting night vision goggle equipment thereon.

Specifically, the cranial headgear includes a flexible plastic temporal strip frame constructed of a temporal strip circumscribing the front and side parts of the cranium above the eyes and ears of the wearer. The temporal strip terminates with ends disposed near the anterior of the cranium. The strip ends include means for anchoring a posterior girth strap which includes centered thereon a webbed pad. The webbed pad is engagable with and somewhat under the occipital protuberance located at the back and lower part of the cranium.

Formed integral with the temporal strip, and located centrally near the forehead region, is a plastic crown strip which extends backwardly over the top of the cranium. The crown strip terminates in a loop through which a Y-shaped strap is anchored. The Y-strap is also connected to the ends of the temporal strip. In another embodiment, the crown strip is directed rearwardly and branches outwardly and downwardly toward the ends of the temporal strip. The branched ends of this crown strip are slotted and connected by other straps to anchor means in the temporal strip ends.

A pair of plastic cheek rests are integral with the temporal strip, and depend downwardly for resting on the cheek bones of the wearer. The cheek bone rests are slotted for anchoring an adjustable chin strap with a bifurcated section engulfing the chin. The chin strip is snap locked to a pair of lower girth straps which are connected to the webbed pad.

In yet another embodiment of the invention the crown strip is eliminated, and the temporal strip is ribbed in the forehead region to prevent torsional twisting movement. In addition, a single strap is directed over the cranial crown and connected to the temporal strip above the wearer's ears.

Various straps of the headgear embodiments are anchored to the plastic temporal strip by plastic anchor brackets solvent bonded thereto. In this manner, none of the straps are sewn directly to the plastic headgear frame, and thus the assembly of the straps and buckles can be accomplished at a remote location without the need of the headgear frame itself.

BRIEF DESCRIPTION OF THE DRAWINGS

Further advantages and features of the present invention will become apparent from a description of the structure thereof, taken in conjunction with the accompanying drawings, in which:

FIG. 4 is a side elevational view of the preferred embodiment of the invention;

FIG. 5 is an isometric view of the headgear embodiment shown in FIG. 4;

FIG. 6 is a cross-sectional view of a strap anchor taken along line 6—6 of FIG. 4;

FIG. 7 is a front elevational view of the strap anchor bracket;

DETAILED DESCRIPTION OF THE INVENTION

Figures 1, 2, 3:
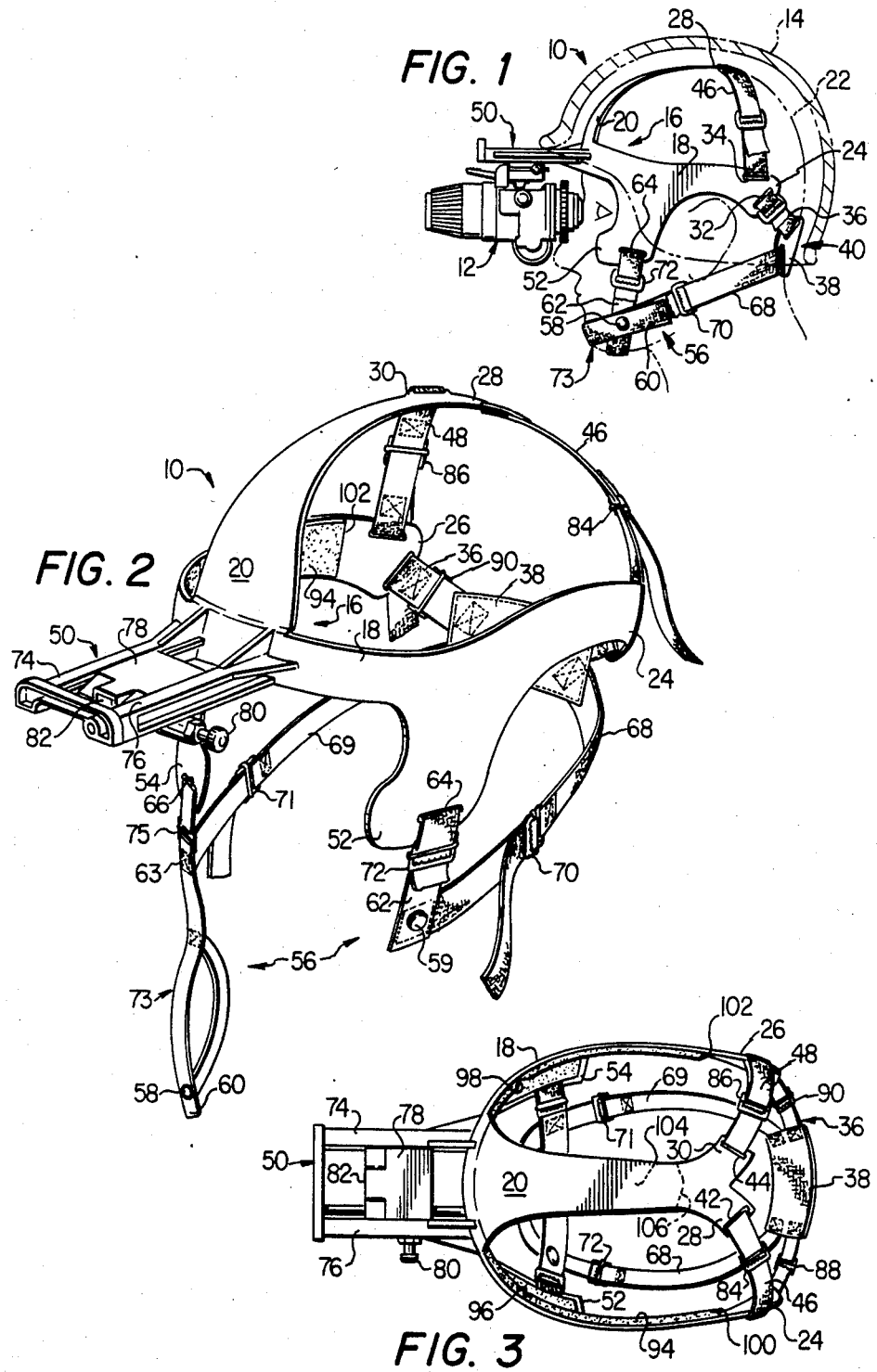
FIG. 1 is a side elevational view of the night vision goggle headgear according to the invention, shown as it would be worn with a goggle, and a combat helmet shown in phantom.
FIG. 2 is an isometric view of the night vision goggle headgear and integral goggle bracket.
FIG. 3 is a top view of the night vision goggle headgear.

The application of the present invention is best understood by referring to FIG. 1 of the drawing. Shown is a headgear, indicated by the reference character 10, which is mounted to the cranium of a wearer so that a night vision goggle 12, fixed to the headgear 10, is held in the wearer's line of sight. With this arrangement, the person wearing the headgear 10 can view objects in the darkness through the goggle 12, and yet have both hands free for other uses.

The night vision goggle headgear 10, constructed according to the invention, is an improvement over the goggle face frames heretofore known. The present invention eliminates pressure points on the sensitive facial tissues by providing headgear engagement on the posterior part of the cranium. By using the configuration of headgear 10, the effective center of gravity of the headgear and attached goggle is shifted backwardly, as compared to prior face frames. In addition, the night vision goggle headgear 10 is compatible with a helmet 14, shown in phantom, or a gas mask (not shown). Because a gas mask or other similar device must conform very closely over the face of the wearer, the night vision goggle headgear 10 is constructed so as to provide minimal interference with the facial area when donned over a gas mask.

In accordance with the invention, the night vision goggle headgear 10 includes a cranial frame 16 comprising a temporal strip 18 and integral crown strip 20. As can be seen from the figure, the cranial frame 16 fits over the upper part of the cranium 22. Temporal strip 18 terminates at ends 24 and 26, the latter not shown in FIG. 1, thereby partially circumscribing the crown of the cranium 22. Various structural elements of the invention are formed in pairs, such as temporal strip ends 24 and 26. Because FIG. 1 only shows the left side of the headgear construction, the other elements of the pairs are understood as forming a part of the right hand side of the invention. Therefore, in the description which follows, both elements of a pair will be identified, even though only one element may be shown in some of the figures.

The crown strip 20 includes a compound curvature at its base for conforming to the cranium. The crown strip 20 extends backwardly over the top of the cranium 22 and branches out into ends 28 and 30. The temporal strip ends 24 and 26 are each double slotted 32 and 34, one slot thereof for anchoring each end of a posterior girth strap 36. In an intermediate position on the posterior girth strap 36 is a webbed pad 38 for engaging the lower edge of the cranial occipital protuberance 40. The occipital protuberance 40 is located at the anterior lowermost part of the cranium 22, the bottom lateral edge of which is disposed substantially in the center of the webbed pad 38, as shown in FIG. 1. The branched ends 28 and 30 of the crown strip 20 include slots 42 and 44 (not shown in FIG. 1), each for anchoring an adjustable radial strap 46 and 48 to respective slots in the temporal strip ends 24 and 26.

Formed integral with the temporal strip 18, and centered in the front thereof, is a goggle mounting bracket 50 for allowing slideable adjustment of the night vision goggle 12 with respect to the wearer's eyes. In order to reduce a concentrated pressure on the wearer's forehead due to the lever action of the goggle 12 on the bracket 50, the crown strip 20 is provided for transferring the downward pull of the goggle 12 backwardly over the crown of the cranium 22. It can be appreciated from FIG. 1 that the pressure of the goggle 12 hanging on the bracket 50 is distributed on the frontal part of the cranium 22 by the crown strip 20, and in addition is transferred to the occipital protuberance through the pair of radial straps 46 and 48, the posterior girth strap 36 and the webbed pad 38. It can also be seen that the engagement of the webbed pad 38 partially under the occipital protuberance 40 prevents the weight of the goggle 12 from pulling the temporal strip 18 into a lowered position on the forehead.

Goggle pressure is also distributed over the cranium 22 by a pair of cheek rests 52 and 54 depending downwardly and formed integral with the temporal strip 18. The cheek rests 52 and 54 aid in preventing the front part of the headgear 10 from being pulled downwardly thus moving the goggle 12 out of the wearer's line of sight. A certain amount of headgear pressure on a person's cheek bones does not cause an undue amount of strain, as there are no major nerves or blood vessels disposed over the surface of the cheek bones.

With the construction of the invention described thus far, a person can quickly don the headgear 10 and goggle 12 to provide night vision. In practice, the goggle 12 is removable from the mounting bracket 50, and is therefore attached after the headgear 10 is donned and secured. For a complete description of the releasable engagement feature, reference should be had to the above-identified related application entitled, "Quick Release Night Vision Goggle". In securing the headgear 10 to the cranium 22, additional fastening straps are provided to maintain engagement thereof to the cranium 22 when the wearer is highly active, such as when running. A lower fastening strap 56 is snappable together near the left side of the chin by a snap 58. A looped end 60 of fastening strap 56 provides a pull tab for disengaging the snap 58 and separating the straps so that the headgear 10 can be removed from the cranium 22. When snapped, the fastening strap 56 assures positive engagement of the webbed pad 38 on the lower edge of the occipital protuberance 40, and assures that the temporal strip 18 cannot move upwardly off the cranium 22.

Specifically, the fastening strap 56 comprises a chin strap 62 which is routed under the chin of the wearer, and anchored at each end thereof in slots 64 and 66 formed in each respective cheek rest 52 and 54. A lower girth strap 68 has ends fastened to the webbed pad 38, and encircles the lower face of the wearer in engagement with the mandible or frontal chin bone. The fastening strap 56 includes a pair of buckles 70 and 72 for providing adjustment of the chin strap 62 and lower girth strap 68. A bifurcated strap section 73 is formed where the chin strap 62 and the lower girth strap 68 engulf the wearer's chin.

The particular construction with which the chin strap 62 and lower girth strap 68 are arranged is shown in more detail in FIG. 2. It is necessary to understand, however, that when the fastening strap 56 is unsnapped by snap 58, the straps are separated for easy donning on the cranium 22 of a wearer. The only loose strap end comprises the looped pull tab end 60. To that end, the integral temporal strip 18 and cranial strip 20 are formed of a stiffly resilient material to thereby provide a noncollapsible structure easily donned without having to untangle a plurality of loose straps. In other words, should an emergency situation suddenly arise, the cranial frame 16 can be situated on the cranium 22, much like a baseball cap, without first having to determine an inside-outside or up-down relationship. It should also be appreciated that for purposes of comfort, the fastening strap 56 need not be snapped to provide engagement of the headgear 10 to the anterior part of the cranium 22. In addition, the entire frontal face area of the wearer remains exposed, thus providing a high degree of compatability with other facial apparatus, such as gas masks. When a gas mask is employed, the bifurcated chin strap section 73 is simply placed over the bottom part of the gas mask, holding the mask in firm contact over the chin of the wearer.

With reference again to FIG. 2, the night vision goggle headgear 10 is shown as it would appear unattached. With regard to the structural aspects of the invention, the integral temporal strip 18, crown strip 20 and cheek rests 52 and 54 are formed of a stiffly resilient plastic, such as a nonglass-filled Ultem plastic. This plastic can be obtained from the General Electric Corporation. Formed integral with the temporal strip 18 is the goggle mounting bracket 50 which includes a pair of spaced-apart rails 74 and 76, with a goggle mounting carriage 78 slideably movable therein. A release button 80 is depressable to allow slideable movement of the goggle mounting carriage 78 along the rails 74 and 76. When the button 80 is released, the goggle mounting carriage 78 remains in a fixed position. The night vision goggle 12 (shown in FIG. 1) is removably engageable in a receptacle 82 formed as part of the goggle mounting carriage 78. While various techniques may be employed for securing the night vision goggle 12 to the headgear 10 of the invention, mounting apparatus ideally suited for the present application is fully disclosed in the above-identified related application entitled, "Adjustable Night Vision Goggle Mounting Bracket".

The thickness of the temporal strip 18 and crown strip 20 vary from the front of the frame 16 rearwardly. The frontal part of the temporal strip 18 adjacent the goggle mounting bracket 50 is about 90–100 thousandths of an inch thick. The temporal strip 18 between the frontal part thereof and the cheek rests 52 and 54, as well as the forward part of the crown strip 20, is about 80 thousandths of an inch thick. As the cranial frame 16 progresses rearwardly, the thickness is reduced to about 70 thousandths. While these dimensions are exemplary of the construction of the cranial frame 16, it should be understood that there is a gradual change in material thickness from the front of the frame 16 to the back thereof. The thickness of each cheek rest 52 and 54 is about 70–80 thousandths of an inch thick.

As noted in FIG. 2, the headgear frame 16 provides an overall shape of the headgear 10 with minimum strap loose ends, thereby minimizing tangling and providing quick and easy donning. The night vision goggle headgear 10 is placed on the wearer's head by first engaging the lower part of the webbed pad 38 under the occipital protuberance 40 (shown in FIG. 1), and then lowering the frontal part of the cranial frame 16 over and onto the forehead region of the wearer until the crown strip 20 lies comfortably on the top of the cranium 22. Because of variations in cranial sizes, the buckles 84 and 86 of top radial straps 46 and 48 can be adjusted for proper placement of the webbed pad 38 with respect to the bottom edge of the occipital protuberance 40. Buckles 88 and 90 associated with posterior girth strap 36 can be similarly adjusted.

Lower girth straps 68 and 69 are adjustable through buckles 70 and 71 to comfortably maintain the proper position of the webbed pad 38, and also to allow sufficient chin movement for eating or speaking. The vertical chin straps 62 and 63 are made adjustable by buckles 72 and 75 such that when the female part of the snap 58 is engaged with the male part 59, the bifurcated chin section 73 is centered on the chin. With this fastening arrangement, the headgear frame 16 is also snuggly engaged on the cranium 22.

In accordance with another aspect of the present invention, there is shown in FIG. 3 a padding material 94 secured to the inside surface of the cranial frame 16. Elastic foam padding of 0.05–0.09 inch foam and covered with a soft nonallergenic leather can be used as the material to cushion the frame 16 on the cranium 22, thereby providing a greater degree of conformance of the headgear 10 to cranial shapes and thus reducing localized areas of pressure. A leather covering is preferable as it is widely considered to be more nonallergenic than certain types of padding materials, such as synthetic foams. A leather of suitable quality may be of the extra soft sheepskin type, chrome tanned and of 1.5–2 ounce weight.

The padding 94 includes recessed areas 96 and 98 located near the temporal areas of the cranium 22 where the temporal nerves and blood vessels are concentrated. With this construction, the temporal strip 18 is not compressed tightly against the temporal nerves and blood vessels, whereby the nerves are not aggravated and the blood flow to the brain is not restricted. Padded headgear of the type described can thus be worn for extended periods of time without causing fatigue or headaches. Of course, it is well within the realm of those skilled in the art to recess or concave a portion of the inside surface of the temporal strip 18 to reduce contact with the temporal area of the wearer's head. The padding 94 extends backwardly along the temporal strip 18 and terminates at 100 and 102. Padding 104 is also adhered to the undersurface of the crown strip 20 and terminated at 106. This allows sufficient room under the terminal ends 24 and 26 of the temporal strip 18 and crown strip 20 for the anchor loops of each strap attached in the respective slots, thereby reducing pressure points on the cranium 22 caused by the looped strap ends.

In FIG. 4 there is shown the preferred embodiment of the invention. The elements shown in this embodiment which are alike or similar to those described above are represented by corresponding reference characters. In this embodiment, the cranial frame 16 includes a crown strip 108 which terminates in a looped end 110. The base part 112 of the crown strip 108 which joins the temporal strip 114 is constructed with a compound curve. By this it is meant that the crown strip base part 112 is somewhat cupped to conform to the upper forehead of the cranium 22. In addition, the temporal strip 114 of the embodiment shown in FIGS. 4 and 5 includes terminal ends 116 and 118 angled downwardly behind the wearer's ears.

A Y-shaped strap 120 is provided for connecting the crown strip 108 to the temporal strip ends 116 and 118. Particularly, the Y-strap includes strips 122, 124 and 126 sewn at juncture 128. Strip 126 has fastened thereto a buckle 130 with a wire loop 132 disposed within the crown strip loop 110. The buckle loop 132 is not continuous, but rather has split ends (not shown) which are inserted within the crown strip loop 110. The split ends are then spread apart and pinched together so as to be concealed within the crown strip loop 110. Y-strap strips 122 and 124 terminate in ends 134 and 136 sewn around loops in a pair of respective anchor brackets 138 and 140. The anchor brackets 138 and 140 are made integral with the Y-strap 120, which strap can thus be constructed separate from the headgear frame 16.

The strap anchor brackets 138 and 140 are constructed of plastic and solvent bonded to the headgear frame 16. The strap anchor brackets 138 and 140 will be described in more detail below. The circumferential temporal size of the headgear frame 16 can be adjusted by a posterior girth strap 142, shown buckled in FIG. 4 and unbuckled in FIG. 5. As noted in the latter figure, girth strap 142 is threaded through temporal strip end slots 144 and 146. The girth strap 142 can thereby be cinched to adjust the fit of the cranial frame 16 as desired, and held fastened by the engagement of the strap end 148 with buckle 150.

The webbed occipital pad 152 is maintained adjacent the occipital protuberance of the wearer's cranium 22 by the posterior girth strap 142 held in engagement with the occipital pad 152 by a loop 154. Loop 154 is sewn to the occipital pad 152, and the posterior girth strap 142 threaded through the loop 154 during initial fitting of the headgear to one's head. The webbed occipital pad 152 is constructed of an outer webbed covering 156, and an inner padded leather covering 158. The two coverings 156 and 158 are sewn together, and to the girth strap loop 154. In addition, the ends of lower girth straps 160 and 162 are sandwiched between the occipital pad coverings 156 and 158 and sewn thereto, such as shown by 164. Each lower girth strap 160 and 162 includes a buckle 166 for adjustment. Moreover, the frontal end of each lower girth strap 160 and 162 is connected to a chin cup 168. On the right hand side of the headgear, the lower girth strap 162 is sewn directly to the chin cup 168. On the left hand side of the headgear, the lower girth strap 160 is sewn to a pull tab strip 170, which strip includes a snap 172. Attached to the chin cup 168 is a corresponding and engaging snap (not shown) for snap locking to the snap 172. With this construction, the end 174 of the pull tab 170 can be yanked upwardly to disengage the snap parts 172, whereby the headgear can be removed upwardly and off the wearer's head.

The pull tab strip 170 is also sewn to a vertical chin strap 176. Vertical chin strap 176 is made adjustable by buckle 178 to thereby adjust the conformance and fit of the top part of the headgear over the crown of the wearer's head. Vertical chin strap 176 is made integral with the cranial frame 16 by another anchor bracket 180. The corresponding vertical chin strap on the right hand side of the headgear is comparably secured to the headgear frame 16.

Provided as a cushioning pad is a soft foam-filled leather forehead strip 177 adhered to the inner surface of the temporal strip 114. A similar cushioning pad 179 is secured to the inner surfaces of the cheek rest pieces 175. As noted in FIG. 4, the cheek rest pieces 175 are somewhat truncated insofar as the forwardly directed tab is eliminated. With this form, the use of a gas mask is facilitated as the facial area of the wearer is substantially unobstructed with the apparatus of the headgear.

The strap anchor bracket 180 is shown in cross section in FIG. 6. The anchor bracket 180 is constructed of a plastic similar to that of the cranial frame 16, both of which are fusible together by a solvent. The anchor bracket 180 includes a back surface 182 to which the solvent is applied for fusing to the temporal strip 114. The anchor bracket 180 is located at a predefined location by a pair of studs 184 and 186 (FIG. 7) pressed into a corresponding pair of spaced-apart holes 188 in the cranial frame 16. Formed along the side edges of the anchor bracket 180 are a pair of support ribs 190 and 192 for reinforcing the bracket structure. The anchor bracket 180 further includes a bail part 194 around which the strap 176 is looped and sewn at 196. The anchor bail part 194 is spaced outwardly away from the inside surface 182 of the bracket to provide a clearance for the strap loop section 198 disposed between the temporal strip 114 and the anchor bail 194.

A frontal view of the strap anchor bracket 180 is shown in FIG. 7. Shown in phantom are the location studs 184 and 186. Also shown are the support ribs 190 and 192 for providing reinforcement to the anchor bail 194, especially when the strap 176 is pulled or yanked in a direction transverse to the surface of the headgear frame 16.

The headgear illustrated in FIGS. 4–7 embodies many of the advantages described in connection with the previously illustrated embodiment. In addition, there is illustrated here a headgear in which the frame part 16 can be conveniently constructed at one manufacturing location and the strapworks at another. The two parts can then be finally assembled by threading the various straps through framework slots, and by adhering the brackets to the predefined locations on the headgear framework. It should be understood that with this arrangement a significant cost advantage can be realized by injection molding the framework locally, and by constructing the strapworks in geographical areas having low labor costs.

Figure 8:
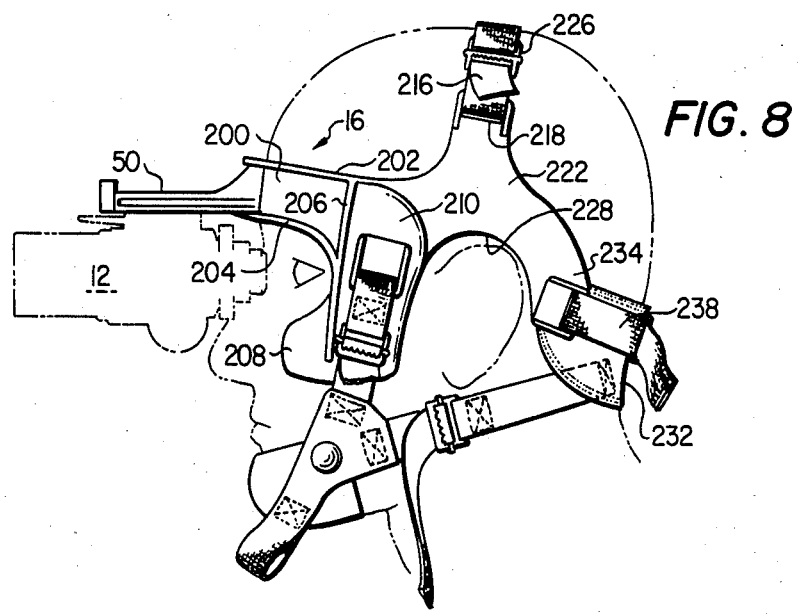
FIG. 8 is a side elevational view of yet another embodiment of the invention.
Figure 9:
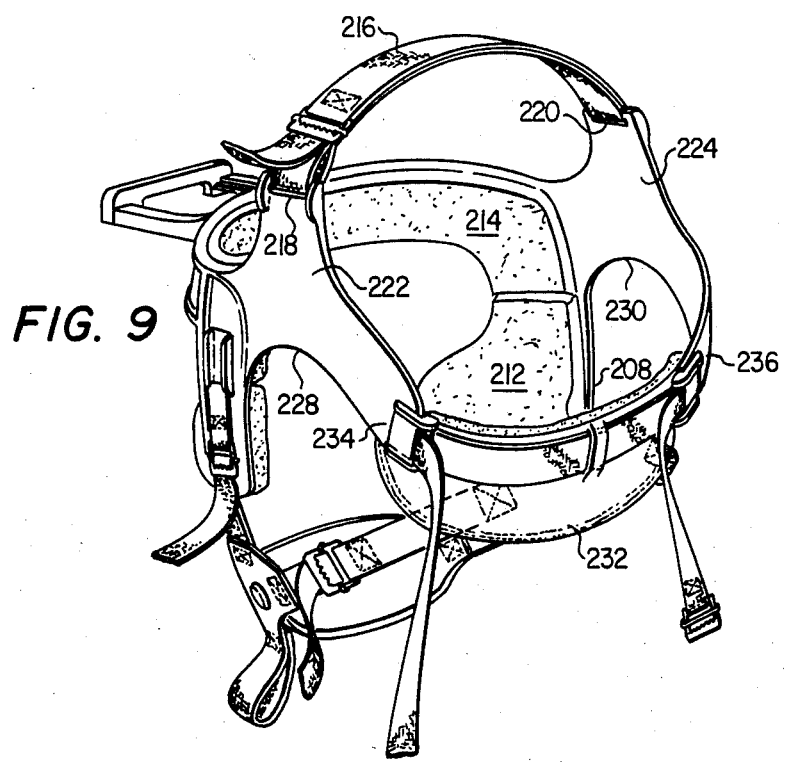
FIG. 9 is an isometric view of the headgear embodiment shown in FIG. 8.

Yet another embodiment of the headgear is illustrated in FIGS. 8 and 9. In this embodiment, the crown strip of the cranial frame 16 is eliminated. Instead, the frontal part of the temporal strip 200 is reinforced by ribs 202, 204 and 206. Ribs 204 and 206 merge together and extend downwardly integral with the cheek rest 208. With this construction, the vision equipment 12 slung from the bracket 50 is fully supported and prevented from torsionally twisting the temporal strip 200.

As shown in FIGS. 8 and 9, a cupped part 210 is provided in the cheek piece 208 and in the side portion of the temporal strip 200 for holding therein a leather-covered foam padding 212. Because of the absence of the crown strip, the padded area 214 provides a substantial surface area for supporting the weight of the vision equipment 12 against the temporal part of a wearer's head. It should be noted from FIG. 9 that the additional padding 214 on the forehead part of the temporal strip 200 provides additional surface area for supporting the pressure due to the weight of the vision equipment 12 mounted on the forehead part of the temporal strip 200.

Support of the headgear over the crown of the cranium 22 is provided by a crown strap 216. The crown strap 216 is threaded through slots 218 and 220 formed in temporal strip extensions 222 and 224. Crown strap 216 is made adjustable by buckle 226. Temporal strip extensions 222 and 224 are formed integral with the temporal strip 200, and are located on the temporal strip above respective ear cutouts 228 and 230. The temporal strip extensions 222 and 224 are formed according to the general curvature of a cranium, and thereby provide added support for the cranial frame 16 on the wearer's head.

It should be noted in FIGS. 8 and 9 that the occipital pad 232 is laterally elongated. Indeed, the occipital pad 232 fits somewhat under the terminal ends 234 and 236 of the temporal strip 200. As described above in connection with the webbed pads, the elongate occipital pad 232 is padded on the inside surface with a leather-covered foam, thereby providing additional comfort and support about the entire bottom edge of the cranial occipital protuberance. The posterior girth strap 238 is connected to the elongate occipital pad 232 by a loop (not shown).

The vision equipment headgear illustrated in FIGS. 8 and 9 includes many of the structural features and advantages described above in connection with the other headgear embodiments. Therefore, the description hereof will not be further encumbered with the description of these structural features.

From the foregoing, the disclosed night vision goggle headgear embodiments provide a substantial improvement over the face frames known in the art. The headgear of the present invention provides a stiffly resilient headgear frame which is shaped to fit over the crown of the cranium. The flexible ends of the headgear frame are coupled together by adjustable straps, one such strap having a webbed pad for engagement about the lower edge of the cranial occipital protuberance. The configuration of head gear 10 then has the effect of moving the center of gravity of the combined headgear and night vision goggle backwardly, thereby reducing muscle stress in the neck and shoulders of the wearer. A pair of cheek rests are molded integral with the headgear frame to allow some of the goggle weight to be supported on the wearer's cheeks. In addition, padding is provided on the inner surfaces of the headgear frame for conforming to different head shapes. The padding includes recessed areas corresponding to the temporal regions of a person's head so as to reduce tension or headaches due to pressure on temporal nerves and blood vessels. While the headgear can be worn on the cranium with the goggles in the wearer's line of sight vision, fastening straps are provided for attaching the headgear about the head using a chin strap. The fastening thereof is optional during general use, and may be necessary during highly active movements. Assembly of the headgear is facilitated with the use of plastic strap anchor brackets to which the straps are fastened by sewing. The final assembly is accomplished by bonding the brackets to the headgear frame at predefined locations.

The various embodiments of the invention are described above in detail with respect to specific structures to illustrate the principles and concepts of the invention. Therefore, various modifications and additions to the night vision goggle headgear are undoubtedly possible by those skilled in the art without departing from the spirit and scope of the invention as claimed hereinbelow. Indeed, those skilled in the art may not find it necessary to adopt all of the various advantages or features of the present invention into a single headgear in order to realize the individual advantages.

What is claimed is:

1. A lightweight headgear device attachable to a wearer's head so as to leave the face of the wearer substantially unobstructed and accommodate the concurrent use of a gas mask, or the like, and adapted for suspending vision equipment proximate the wearer's eyes, comprising:
   a cranial frame having a strip of material at least partially encircling the crown of the wearer's head above the wearer's ears, said strip having a pair of free ends which are angled downwardly behind the wearer's ears near the cranial posterior;
   a vison equipment support member engageable with a frontal part of said frame; and
   head engaging means engageable with the cranial occipital protuberance of the wearer's head, said head engaging means being connected between the free ends of the cranial frame so as to be disposed adjacent the cranial occipital protuberance and such that movement of the headgear occasioned by the weight of the vision equipment is counteracted by the engagement of the head engaging means with the cranial occipital protuberance.

2. The headgear device of claim 1 further including a crown strip integral with said cranial frame and engageable with the crown of the cranium, and including strap means connected thereto and to the free ends of said cranial frame.

3. The headgear device of claim 2, wherein said crown strip includes a branched end, and said strap means comprises two straps, each strap connected between one branched end of said crown strip and one free end of said cranial frame.

4. The headgear device of claim 2 wherein said strap means includes a Y-shaped strap connecting the free ends of said cranial frame to said crown strip.

5. The headgear device of claim 1 further including cheek rest means integral with said cranial frame and depending downwardly therefrom so as to be disposed proximate the cheeks of the wearer's head.

6. The headgear device of claim 5 wherein the cheek rest means are disposed in front of the wearer's ears, and the free ends of said cranial frame are disposed essentially behind the wearer's ears.

7. The headgear device of claim 1 further including fastening strap means connected to said head engaging means and engageable with the wearer's chin to thereby stabilize the head engaging means in contact with said occipital protuberance.

8. The headgear device of claim 5 further including strap means connected to said head engaging means and to said cheek rest means and engageable with the wearer's chin.

9. A lightweight compact headgear device adapted for supporting vision equipment proximate the eyes of a wearer, and adapted for engaging the top portion of the wearer's head so that the face of the wearer is free from the headgear device such that the wearer can also concurrently wear a gas mask, or the like, comprising:
   a thin cranial frame having a crown strip and left and right temporal strips, each said strip converging and connected together at a juncture proximate the forehead of the wearer, each said strip having a free end terminating near the posterior of the cranium, each said temporal strip having said free ends extending downwardly and substantially behind the wearer's ears, said cranial frame being formed so as to rest on the wearer's head in a position generally above the wearer's ears;
   means for mounting the vision equipment to the juncture of said strips, said mounting means being molded integral with said strips at said juncture;
   first strap mens for connecting the free end of said crown strip to the free end of said left and right temporal strips; and
   second strap means for connecting the downwardly angled free end of said left temporal strip to the downwardly angled free end of said right temporal strip so that said second strap means is disposed in a position so as to be engageable with a posterior portion of the wearer's cranium.

10. The headgear of claim 9 further including a pad attached centrally to said second strap means, said pad for engaging the occipital protuberance.

11. The headgear of claim 10 wherein said pad includes a loop through which said second strap means is inserted.

12. The headgear of claim 10 wherein the free end of said left and right temporal strips includes fastening means for fastening said second strap means so that said second strap means is angled somewhat downwardly and rearwardly toward said occipital protuberance.

13. The headgear of claim 12 wherein said fastening means comprises a slot in the free end of each said left and right temporal strip, each said slot being at an angle with respect to a vertical axis.

14. The headgear of claim 13 wherein said slot is angled at about 45 degrees.

15. The headgear of claim 12 wherein said fastening means includes an anchor bracket fastened to said second strap means and bonded to said cranial frame.

16. The headgear of claim 15 wherein said anchor bracket and said frame include location defining means for locating said bracket to said frame at a predefined location.

17. The headgear of claim 10 wherein said pad is generally rectangular in shape, the second strap means is connected adjacent a top corner thereof, and further including chin strap means engagable with the chin of the wearer and fastened to a bottom corner of said pad.

18. The headgear of claim 17 further including a pair of cheek rests integral with a respective said temporal strip and depending downwardly therefrom and terminating adjacent the cheeks of the wearer, and including strap means for connecting each said cheek rest to said chin strap means.

19. The headgear of claim 9 further including a pair of cheek rests, each integral with a respective said temporal strip and depending downwardly therefrom terminating adjacent a cheek of the wearer.

20. The headgear of claim 9 wherein the crown strip and left and right temporal strips are formed with a thickness that decreases from the juncture thereof to the free ends.

21. The headgear of claim 9 further including a padding adhered to the undersurfaces of said crown strip and left and right temporal strips, said padding including recesses at predetermined locations for conforming to the shape of the cranium.

22. The headgear of claim 9 further including a vision equipment frame fixed to said cranial frame at the juncture of said strips, said vision equipment frame including means for fastening thereto said vision equipment.

23. The headgear of claim 22 wherein said vision equipment frame is molded integral with said cranial frame.

24. The headgear of claim 23 wherein said cranial frame includes a support rib for preventing torsional twisting of the cranial frame due to the weight of the vision equipment.

25. The headgear of claim 24 wherein said cranial frame includes cheek rest means integral thereto, and said support rib is disposed about a forehead area of the cranial frame and onto said cheek rest means.

26. The headgear of claim 9 wherein said crown strip includes a compound curve near the juncture thereof and extending to the temporal strips, said compound curve being slightly cupped to generally conform to a cranium.

27. The cranial headgear of claim 1 wherein the thickness of said temporal strip and said crown strip is greater at the juncture than at said ends.

28. The cranial headgear of claim 27 Wherein said thickness gradually decreases from said juncture to the ends.

29. A lightweight cranial headgear adapted for supporting thereon vision equipment, and adapted for attachment to a wearer's head so as to leave the facial area of the wearer substantially unobstructed such that gas mask equipment, or the like, can also be worn, comprising:
   a flexible temporal strip with ends, and formed to at least partially encircle the temporal area above the ears of a wearer's head, and each said free end being angled downwardly behind the wearer's ears;
   a flexible crown strip joined to the center of the temporal strip, and with an end directed rearwardly;
   means fixed to said temporal strip for supporting thereon the vision equipment;
   a first adjustable strap formed in a Y and connecting the ends of the temporal strip and the end of the crown strip;
   a second strap engageable with the occipital protuberance of the wearer's cranium such that movement of the headgear occasioned by the weight of the vision equipment is counteracted by the engagement of said second strap with the cranial occipital protuberance;
   means for fastening the second strap between the downwardly angled ends of said temporal strip so that said second strap is disposed adjacent said occipital protuberance; and
   third strap means for securing the temporal strip and said crown strip snugly about the wearer's cranium.

30. The cranial headgear of claim 29 wherein said temporal strip is formed in a circular shape conforming generally to a human cranium, and said crown strip includes a compound curved area also conforming generally to the curvature of the cranium.

31. The cranial headgear of claim 29 wherein the ends of the temporal strip are angled inwardly so as to conform to the general lateral curvature of a wearer's head.

* * * * *